(12) United States Patent
Wiek

(10) Patent No.: US 9,352,344 B2
(45) Date of Patent: May 31, 2016

(54) METERING DEVICE

(75) Inventor: Hans-Dieter Wiek, Hochdorf (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 0 days.

(21) Appl. No.: 13/414,241

(22) Filed: Mar. 7, 2012

(65) Prior Publication Data

US 2012/0241467 A1    Sep. 27, 2012

(30) Foreign Application Priority Data

Mar. 23, 2011   (DE) .......................... 10 2011 005 996

(51) Int. Cl.
| | |
|---|---|
| B05B 7/24 | (2006.01) |
| A61C 19/00 | (2006.01) |
| B05B 7/12 | (2006.01) |
| G01F 11/02 | (2006.01) |

(Continued)

(52) U.S. Cl.
CPC ............. *B05B 7/2494* (2013.01); *A61C 19/002* (2013.01); *B05B 7/1254* (2013.01); *B05B 7/1272* (2013.01); *B65D 83/52* (2013.01); *G01F 11/021* (2013.01); *G01F 11/04* (2013.01); *G01F 22/02* (2013.01); *B05B 12/02* (2013.01); *B65D 83/62* (2013.01); *Y10T 137/0318* (2015.04)

(58) Field of Classification Search
CPC ...... A61C 19/002; B65D 83/44; B65D 83/62; B05B 12/02; B05B 7/2494; B05B 7/1272; F01B 17/02; G01F 11/024; G01F 11/021; G01F 11/04; G01F 22/02; A61L 2/00; Y10T 137/0318; Y10T 137/0402

USPC ......... 222/386.5, 105, 394, 148, 189.06, 334, 222/309, 504, 261–263, 149, 249, 250, 495, 222/1; 210/257.1, 257.2, 254, 136, 808; 417/403, 402, 401, 317, 318; 433/88

See application file for complete search history.

(56) References Cited

U.S. PATENT DOCUMENTS

| | | | | |
|---|---|---|---|---|
| 2,770,394 A | * | 11/1956 | Mueller | ............................ 222/1 |
| 3,500,753 A | * | 3/1970 | Greene, Jr. | .................... 417/403 |

(Continued)

FOREIGN PATENT DOCUMENTS

| | | |
|---|---|---|
| DE | 3941430 A1 | 6/1991 |
| EP | 0017036 A1 | 10/1980 |

(Continued)

OTHER PUBLICATIONS

Office Action in EP Application No. 12 155 803.5 dated Apr. 13, 2015.

*Primary Examiner* — Frederick C Nicolas
*Assistant Examiner* — Bob Zadeh
(74) *Attorney, Agent, or Firm* — Marshall, Gerstein & Borun LLP

(57) ABSTRACT

A metering device removes a medium from a pressurized medium container. The metering device includes a metering container which is designed to measure off a quantity of the medium and which has a first region and a second region. The first region is separated from the second region by a movable separating element. The separating element has a first contact face, which is directed towards the first region and delimits or closes off the first region. The separating element also has a second contact face, which is directed toward the second region and delimits or closes off the second region. The first contact face and the second contact face have different surface dimensions.

14 Claims, 5 Drawing Sheets

Figure 1:
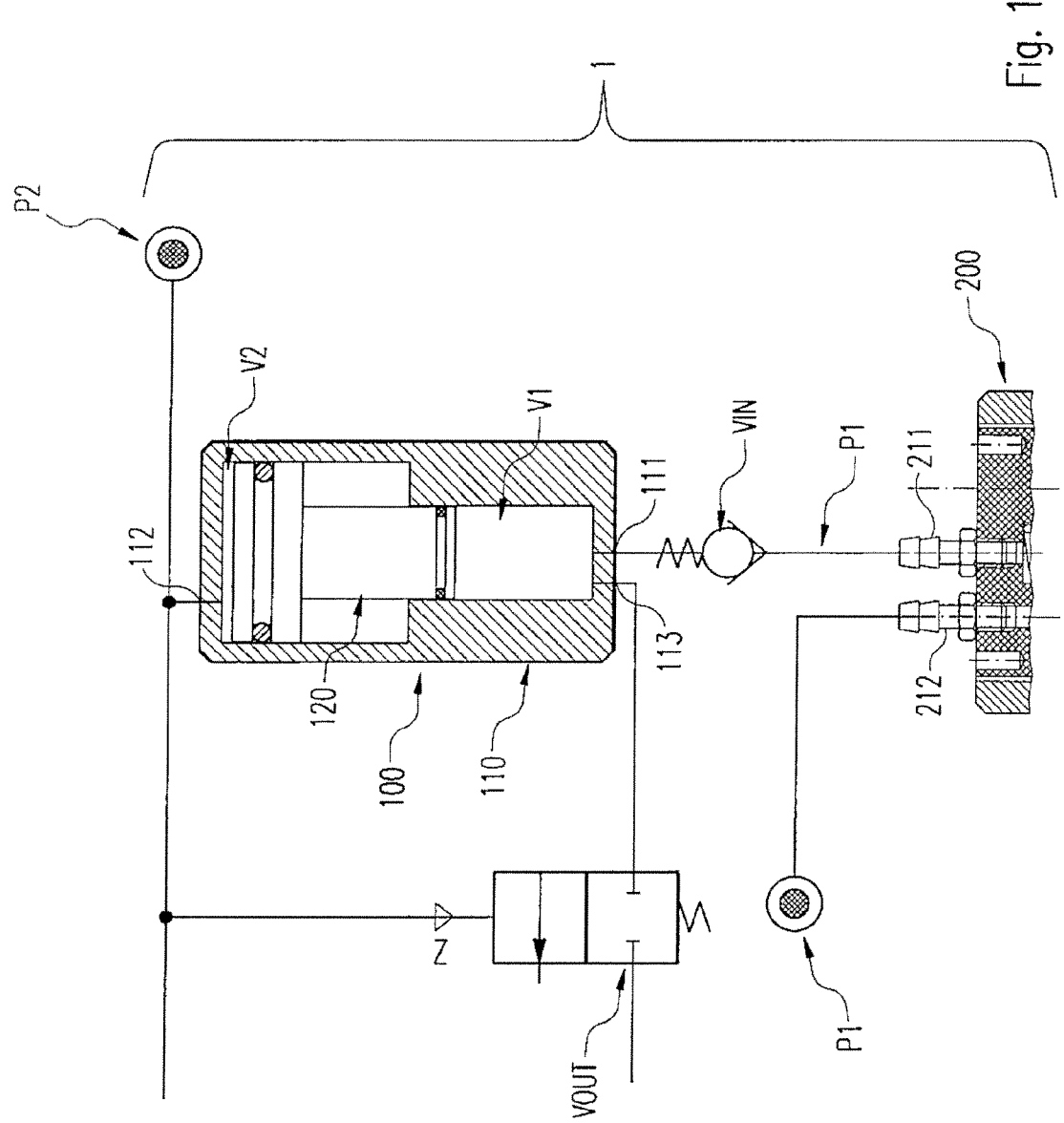

(51) Int. Cl.
  *G01F 11/04* (2006.01)
  *G01F 22/02* (2006.01)
  *B65D 83/52* (2006.01)
  *B05B 12/02* (2006.01)
  *B65D 83/62* (2006.01)

(56) References Cited

U.S. PATENT DOCUMENTS

| | | | |
|---|---|---|---|
| 3,933,652 A * | 1/1976 | Weichselbaum et al. | 210/446 |
| 4,229,143 A * | 10/1980 | Pucher et al. | 417/53 |
| 4,348,160 A * | 9/1982 | Heyneman | 417/403 |
| 4,936,486 A * | 6/1990 | Kummerer | 222/42 |
| 4,990,087 A * | 2/1991 | De Rocchis et al. | 433/104 |
| 5,380,369 A * | 1/1995 | Steinhauser et al. | 134/1 |
| 5,415,248 A * | 5/1995 | Eibl | A61C 19/002 184/55.1 |
| 5,524,797 A * | 6/1996 | Schultz, Sr. | 222/334 |
| 5,705,107 A * | 1/1998 | Kaneishi et al. | 264/40.3 |
| 5,829,633 A * | 11/1998 | Emmerich et al. | 222/1 |
| 5,944,045 A * | 8/1999 | Allen et al. | 137/240 |
| 6,217,329 B1 * | 4/2001 | Eibofner et al. | 433/104 |
| 6,220,242 B1 * | 4/2001 | Wallin | 128/203.12 |
| 2002/0043215 A1 * | 4/2002 | Yoshioka et al. | 118/715 |
| 2003/0133810 A1 * | 7/2003 | Leppin et al. | 417/254 |
| 2008/0145251 A1 * | 6/2008 | Haertl | 417/545 |
| 2012/0267327 A1 * | 10/2012 | Candelora et al. | 210/808 |
| 2012/0298151 A1 * | 11/2012 | Heckenberger et al. | 134/94.1 |

FOREIGN PATENT DOCUMENTS

| | | | |
|---|---|---|---|
| GB | 2180302 | * 3/1987 | F04B 5/00 |
| JP | 2003054662 A | 2/2003 | |
| WO | WO-2011/101396 A1 | 8/2011 | |

\* cited by examiner

METERING DEVICE

BACKGROUND OF THE INVENTION

1. Field of the Invention

The invention relates to a metering device for removing a medium from a pressurized medium container, wherein the medium is provided in particular for the maintenance of medical instruments.

2. Related Technology

In medical technology, the exact metering of media is essential to be able to successfully carry out a treatment or another work procedure. This also applies, among other things, to the metering of media for disinfection, cleaning and maintenance of medical appliances, particularly when these are in direct contact with a patient. Account must be taken of many kinds of interactions which, in some circumstances, can even pose a danger to the life of the person being treated. For example, incorrect metering of a medium used for the cleaning and maintenance of medical appliances could result in an inadequate disinfection or in dilution or neutralization of a treatment agent.

Moreover, in the case where care agents are being metered, it is also necessary to bear in mind that a reliable function of the medical appliance has to be ensured over a long period of time, with minimization of the work involved in servicing. All of these peripheral conditions and requirements result in the need for small quantities of a medium to be able to be metered in a precise manner and discharged exactly at a defined time.

For this purpose, metering containers are known which have a hollow space whose volume is dimensioned such that it can take up exactly the quantity of medium that is to be metered. However, when filling with gases, it is necessary that, in addition to the temperature of the gas, the filling pressure of this hollow space must also be kept within narrow tolerances.

If it is intended to couple a closed and pressurized medium container to the metering container, then the problem additionally arises that the pressure at which the medium reaches the metering container decreases with the number of cycles of removal of medium from the medium container. Particularly with compressible media, the metered quantity of medium can be kept constant only with difficulty.

SUMMARY OF THE INVENTION

The invention provides a metering device and a method, which allow an exact quantity of medium to be discharged at a specific time and with which the complexity of the metering device and its handling and operational safety are optimized.

According to the invention, a metering device is provided for removing a medium from a pressurized medium container, with a metering container designed to measure off a quantity of the medium and which has a first region and a second region, wherein the first region is separated from the second region by a movable separating element. Moreover, the separating element has a first contact face, which is directed towards the first region and delimits or closes off the first region, and a second contact face, which is directed towards the second region and delimits or closes off the second region. Moreover, the first contact face and the second contact face have different surface dimensions.

A contact face is to be understood in particular as meaning the surface portion or surface portions via which the separating element can be brought into contact with a medium that can be introduced into the first or second region.

With the aid of different surface dimensions of the first and second contact faces, a metering device can be obtained with a separating element that experiences a difference force, which occurs at an identical pressure in the first and second regions, that is to say at the so-called equilibrium pressure. A further degree of freedom in the possibilities of controlling the metering device is thus obtained, making it possible safely to adjust a control state of a metering device without a pressure difference between two media. It is thus possible to reduce the number of different pressures that the media need to have for operating the metering device. In this way it is possible, for example, to do without additional pumps or other conveying means or secondary pressure generators for a medium that is to be measured off and, in addition, there is improved operational reliability and increased precision of the metering, since in particular the number of interacting components and the process steps leading to the metering are reduced (convolution of the expected values of the process steps, reduction of the normal distribution range).

According to another aspect of the invention, a metering device is provided for removing a medium from a pressurized medium container, with a metering container which is designed to measure off a quantity of the medium and which has a first region and a second region, wherein the first region is separated from the second region by a movable separating element. Moreover, the metering device is designed in such a way that, at the equilibrium pressure that acts identically on boundary surfaces of the first and second regions, the separating element experiences a force effect that is proportional or inversely proportional to the equilibrium pressure.

In addition to the reduction in the number of possible factors influencing the quality of the metering device, a difference force that is proportional or inversely proportional to the pressure also allows the speed of a work cycle of the metering device to be easily adjusted, which in turn results in simpler control of the metering device.

In addition, particularly in the case of compressible media, a difference force that is proportional to the equilibrium pressure can, with the aid of a counterforce that counteracts the difference force, establish a self-regulating system, so that fluctuations or a decrease in the pressure of the medium that is to be measured off are compensated by adjusting or increasing the volume to be measured off, and the quantity of substance measured off is kept constant. The counterforce could, for example, be generated by compression of a medium in a control region, which is preferably determined by the separating element or to which the separating element is connected. In particular, this applies to the separating element a force that is indirectly proportional to the equilibrium pressure.

The first or second region is preferably designed as a hollow space in the metering container, wherein in particular the separating element is movable so that the volumes or expanse of the two regions or hollow spaces in relation to each other can be altered by the movement of the separating element. Particularly preferably, a movement of the separating element corresponds to the enlargement of the first region with a simultaneous decrease in size of the second region, and a return movement of the separating element corresponds to an analogous recovery of the first and second regions.

Particularly preferably, at least one of the first and second regions is designed so that, in a limit position of the separating element, a volume that is to be determined and measured off in respect of a quantity of medium that is to be metered coincides with the volume of at least one of the first and second regions.

In addition, provision can also be made that a volume that is to be determined and measured off is established only by the movement range of the separating element between two limit positions. In one development, provision can be made that at least one of the limit positions is adjustable.

Particularly preferably, the separating element is substantially freely movable in the metering container. In this case, substantially is to be understood as meaning that the contact faces of the separating element with the metering container are negligible in relation to the surface of the separating element, that is to say, for example, they occupy less than one fifth of the surface of the separating element, and are preferably limited to sealing elements. In one development, two spatially separate sealing elements can be provided.

The position of the separating element at equilibrium pressure is preferably established such that the volume to be measured off or metered is driven out of the metering container, i.e. the separating element reaches a limit position in which the region designed for the measuring-off or metering of the medium is minimized. Here, minimized is to be interpreted as meaning that no movement range of the separating element is available permitting a decrease in size of the corresponding region.

Thus, a simple way by which the medium to be measured off can be driven out of the metering container is established by the fact that an identical pressure is produced in the first and second regions.

In one development of the invention, the separating element is formed by a piston, which is freely movable at least partially in a bore of the metering container. In particular, by means of an advantageous geometry of the contact faces, which preferably have a round, elliptic or polygonal shape, it is also easily possible to establish the magnitude of the difference force. The contact faces preferably also have a different shape from each other.

A further aspect of the invention concerns a metering device for removing a medium from a pressurized medium container, with a metering container which is designed to measure off a quantity of the medium and which has a first region and a second region, wherein the medium container contains a plurality of media separate from each other, in particular at least a first medium and a second medium, wherein the first medium communicates with the first region in such a way that the medium can enter the metering container, and the second medium has a pressure that acts on the first medium in such a way that the first medium enters the metering container, and the metering container is preferably designed to drive the first medium out of the metering container with the aid of the pressure.

It is thus particularly advantageous that one of the media, in this case the second medium, represents a pressure reference, which can be used for a large number of control functions of the metering device. In addition to the advantage already explained, namely that the number of different interacting process steps and parameters can thus be reduced, it is thereby also possible that the pressure of the first medium to be metered is kept almost constant in the medium container, so that the precision of the metering is also thereby improved.

In one development, for example, the possibility of the pressure change between the first and the second medium could be provided such that, in the event of a significant pressure increase of the second medium in relation to the first medium, virtually no change can be perceived in the pressure taken up by the first medium.

Moreover, to keep the pressure of the first medium constant, provision could be made that the quantity or volume of the first medium in the medium container is smaller than the quantity or volume of the second medium. The quantities of medium or the volumes preferably differ from each other by a factor of 2 to 5.

In addition, other possible ways of keeping the pressure of the first medium constant are conceivable.

To this end, in one development of the inventive concept, both the metering container and also the medium container, in addition to having connectors forming a connection between the medium container and the metering container, also have an additional medium connector. The latter can, in the case of the medium container, be used for example for the filling with a medium, so that, with the aid of the medium connector, the pressure of a medium can be kept within defined tolerance limits and, for example when the pressure drops below a threshold value, a medium can be again introduced into the container. This medium can in particular be the second medium, so that the range of fluctuation of a reference pressure represented by the pressure of the second medium can thus be reduced, and the metering precision is thereby decisively improved.

It is particularly advantageous now if the reference pressure of the second medium can be transferred into the second region of the metering container via the additional medium connector of the metering container.

For example, the additional connector can also be connected to a common supply line.

In a preferred embodiment of the invention, at least one of the first and second regions has an inlet opening and, preferably spatially separate from the latter, an outlet opening. Provision can particularly advantageously be made that the inlet opening is connected to a first valve, and for example the outlet opening to a second valve. In one development, the working pressures of the first and second valves differ from each other. The first valve is preferably designed as a non-return valve.

A further aspect of the invention concerns a medium container for a maintenance appliance for the cleaning or maintenance of medical instruments, with a receiving space for a first medium for the maintenance or cleaning of medical instruments, and with a receiving space for a second medium, wherein the receiving space for the first medium is in pressure exchange with the receiving space for the second medium, and the receiving space for the first medium can be emptied with the aid of an external pressure, which acts on the receiving space for the second medium.

Thus, in particular, the transport of the medium container can be made easier, and the outlay in supplying a maintenance appliance with media can be optimized. The application of an external pressure to the second medium creates the possibility of pressure-free production, pressure-free storage and pressure-free transport of the medium container. In addition, the medium container can be easily refilled with the first medium. Moreover, an environmentally friendly medium, for example compressed air, can be chosen as the external pressure source or as the second medium.

One development of the invention involves combining the metering device according to the invention with a maintenance appliance for medical appliances. To this end, it is advantageous to accommodate the metering device and the maintenance appliance in a common housing or to provide a common base plate for this purpose.

Moreover, the combination of an above-described medium container can also be provided in the maintenance appliance for medical appliances. In this case, no additional safety measures are necessary for the care agent container in the maintenance appliance, since the medium container can be kept pressure-free after the maintenance appliance has been switched off. Therefore, after the maintenance appliance has been switched off, a pressure-free medium container can be obtained, in particular a care agent can or spray can, with a first receiving space for a first medium, which for example receives a care agent or maintenance oil, which container can be emptied only by application of external pressure.

The metering device is particularly preferably designed for measuring off a care agent for medical instruments, in particular dental instruments.

In one illustrative embodiment of the invention, the metering container is connected to an atomizer for the medium to be metered, which for example delivers a care agent to a dental instrument, in particular to the interior of the dental instrument.

In the context of the inventive concept, provision can additionally be made that the atomizer is connected to a compressed-air connector, wherein the metering container is preferably likewise connected to the compressed-air connector. For example, this can be a connection to the second region of the metering container.

Moreover, it is likewise conceivable that the compressed-air connector is connected to the additional medium connector of the medium container, and thus a reference pressure can be introduced both into the metering container and also into the medium container via the second medium, in this case the compressed air.

In addition, the compressed-air connector could be connected to the second valve, which is connected to the outlet opening of the metering container.

In addition to the compressed air described, the second medium can easily be provided in the form of other pressurized media, for example nitrogen or carbon oxides, so that the pressure of the second medium forms a reference variable or a reference pressure that controls a large number of components of the maintenance system, in particular the metering device and the atomizer, as a result of which the range of fluctuation of the maintenance process is in turn reduced on account of the reduced number of the interacting parameters or components, and the maintenance result can be optimized.

It is stressed that a pressure or a force is made available directly through the medium, and this, for example, goes beyond the use of electricity which, to generate a force, always requires a converter, the efficiency of which is also generally very poor.

This is clear in particular in a further aspect of the invention. This concerns a method for removing a medium from a pressurized medium container, with a metering device according to the invention. The method comprises the steps of transferring a medium from the medium container into a first region of the metering container until the first region is completely filled, and driving the medium out of the metering container by filling the second region with a medium, preferably another medium.

The transfer of the medium from the medium container into the first region of the metering container can take place with the aid of the pressure of the first medium, in this case a maintenance oil, present in the medium container. The separating element is moved in such a way that the first region experiences a change in size or expanse, which change corresponds to the quantity of the medium that is to be measured off. Moreover, in this case provision can be made that the pressure of the first medium is established by interaction with a second medium in the medium container, in this case compressed air.

The expulsion from the medium container by a second, preferably different, medium, in this case compressed air, can be effected by applying an identical pressure to the second region of the metering container.

In a preferred development, provision is made in particular that the pressure at which the other medium is introduced into the metering container does not exceed the pressure at which the medium is introduced into the metering container.

After the first medium has been measured off and driven out of the metering container, the first medium can then be delivered, for example, to an atomizer, which atomizes the first medium. The operation of the atomizer, in particular the atomization, can take place with the aid of the second medium, so that, on the one hand, the metering can be carried out substantially for a liquid medium whose volume remains almost independent of pressure fluctuations. On the other hand, the second medium can be kept gaseous and thus contribute at the same time to the foaming or atomization of the first medium in the atomizer, wherein the second gaseous medium provides said reference variable or reference pressure that operates and controls the maintenance device.

A further aspect of the invention concerns a method for operating a disinfection and maintenance appliance for dental instruments, wherein a common pressurized second medium is used to control a metering device for a first medium and at least one further device for discharging a first medium.

It must also be noted that, as will be clear from what has been described above, a combination of the developments of the invention and of the various aspects of the invention is not excluded.

BRIEF DESCRIPTION OF THE DRAWINGS

The invention is explained in more detail below with reference to the attached drawings, in which identical elements are provided with the same reference signs in all the figures. In the drawings:

FIG. 1 shows an illustrative embodiment of a metering device according to the invention;

FIG. 2 shows a detailed view of a metering container;

FIG. 3 shows another detailed view of a metering container;

FIG. 4 shows a detailed view of a medium container; and

FIG. 5 shows an example of a combination of a metering device according to the invention and an atomizer in a dental maintenance appliance.

DETAILED DESCRIPTION

Medical or dental handpieces are tubular parts that the physician or dentist grips as a gripping sleeve during treatment. A handpiece conventionally used in dentistry is what is known as a drill handpiece, which at its front end carries a treatment tool, in particular a drill, and at its rear end is coupled to a supply hose by means of a coupling. Power supply lines for driving the treatment instrument and fluid lines for treatment media, for example air and/or water, run through the handpiece. A distinction is often made between what are called turbine handpieces, in which compressed air is provided to supply a turbine arranged in the front end region, and what are called motor handpieces, which have an electric motor as the drive unit.

To prolong the function of the handpieces, it is necessary from time to time to carry out maintenance, in particular of the rotatably mounted drive elements. Moreover, the ever increasing hygiene demands in dentistry mean that handpieces have to be serviced at regular intervals. Successful servicing and compliance with the relevant regulations have to be fully documented by the dentist, which entails considerable cost in terms of personnel and also organization.

Automatic servicing by machine, with the aid of a cleaning and maintenance system, satisfies the requirement, in dental practices and hospitals, for reliable and reproducible cleaning and maintenance of handpieces, angled pieces, turbines, collets or other dental instruments which in particular require internal cleaning and maintenance with oil.

A suitable cleaning and maintenance system performs, for example, the following cleaning and maintenance sequence, which in particular also involves the internal cleaning and maintenance of the dental instruments.

In a parallel maintenance sequence, each instrument undergoes separate cleaning, in particular to permit specific internal cleaning. For the internal cleaning, a so-called "clean solution" is first of all metered and, atomized as a mist, is introduced into an interior of the instrument, for example a transmission channel or spray channel of a handpiece. The atomization for introducing the mist into the dental instrument is carried out with the aid of compressed air, which is prepared according to EN-ISO07494-2. In addition, the compressed air can likewise be used, during the time of action of the "clean solution", to move the latter within the dental instrument. When the time of action has ended, the dental instrument is flushed with deionized water which, for example, has a conductivity of less than 50 µs. The deionized water is then blown out by means of said compressed air, it being possible for the described steps to be adapted and optimized, for example in terms of time, number of repetitions, quantity of media or control of the compressed air, to specific instruments or combinations of instruments that are to be cleaned.

When the cleaning is completed, a maintenance step, in particular oil lubrication, is carried out individually for each dental instrument, to be able to supply a precisely metered quantity of care agent to the instrument. The care agent, likewise atomized as a mist, is introduced into the interior of a dental instrument, for example a transmission channel. In the same way as with the described cleaning, compressed air is likewise used for the atomization; after the maintenance step is completed, the instrument is simply blown out with compressed air. To improve the displacement of excess oil, this can also be done in pulses. Provision can be made in particular that the metering of the care agent is optimized by means of a timed control.

The cleaning and maintenance appliance affords the possibility of preparing several dental instruments simultaneously. A so-called "state machine" allows the control sequences provided individually for each dental instrument to be coordinated in such a way that time optimization is achieved.

For the operation of the above-described cleaning and maintenance appliance, the following in particular are provided: compressed air at 4-6 bar and a volumetric flow of >50 l/min prepared according to EN-ISO7494-2, maintenance oil (dental oil), "clean solution", deionized water (conductance <50 µs), and power supply at 100-240V AC (50-60 Hz).

It will be clear in particular that, in this illustrative embodiment, the media "clean solution" and "maintenance oil" are to be metered, and the medium "compressed air" contributes substantially to the common control and the operation of the components of the maintenance system. In the chosen illustrative embodiment, the media "clean solution" and "maintenance oil" thus represent a first medium M1, which in this case is liquid, and the medium "compressed air" represents a second medium M2, which is gaseous in the illustrative embodiment described.

A precise metering of the quantity of the media to be supplied to the respective instrument contributes to an optimization of the cleaning and maintenance quality and additionally promotes the time sequence of the described steps, for example by a reduced blow-out time of the maintenance oil, since the quantity of the excess oil is optimized.

The maintenance appliance therefore comprises a metering device 1 for removing a medium M1 from a pressurized medium container 200.

As is clear from FIG. 1, the metering device 1 according to the invention has a metering container 100, with a first region V1 and a second region V2, wherein the first region V1 is separated from the second region V2 by a movable separating element 120.

The maintenance system also comprises a pressurized medium container 200, which is in medium exchange with the metering container 100. The use of a pressurized medium container 200 does away with the need for additional pumps or for a large number of actuating means for conveying and delivering the media, with the result that the complexity of the maintenance appliance in terms of its structure and operation can be reduced. In addition to the aforementioned improvement in metering, the likelihood of incorrect operation can in particular also be minimized in this way.

The maintenance system preferably has a medium container 200 which contains a plurality of media M1, M2 separate from each other, namely at least a first medium M1 and a second medium M2, wherein the first medium M1 communicates with the first region V1 of the metering container 100 in such a way that the medium M1 can enter the metering container 100, and the second medium M2 has a pressure P1 that acts on the first medium M1 in such a way that the first medium M1 enters the metering container 100. Thus, the pressure P1 of the medium M2 can serve to establish a reference point of the pressure synchronization and, as has already been indicated, can control or operate many other components of the maintenance system. In particular, the pressure P1 can itself be sufficient to drive the first medium M1 out of the metering container 100.

Figure 4:
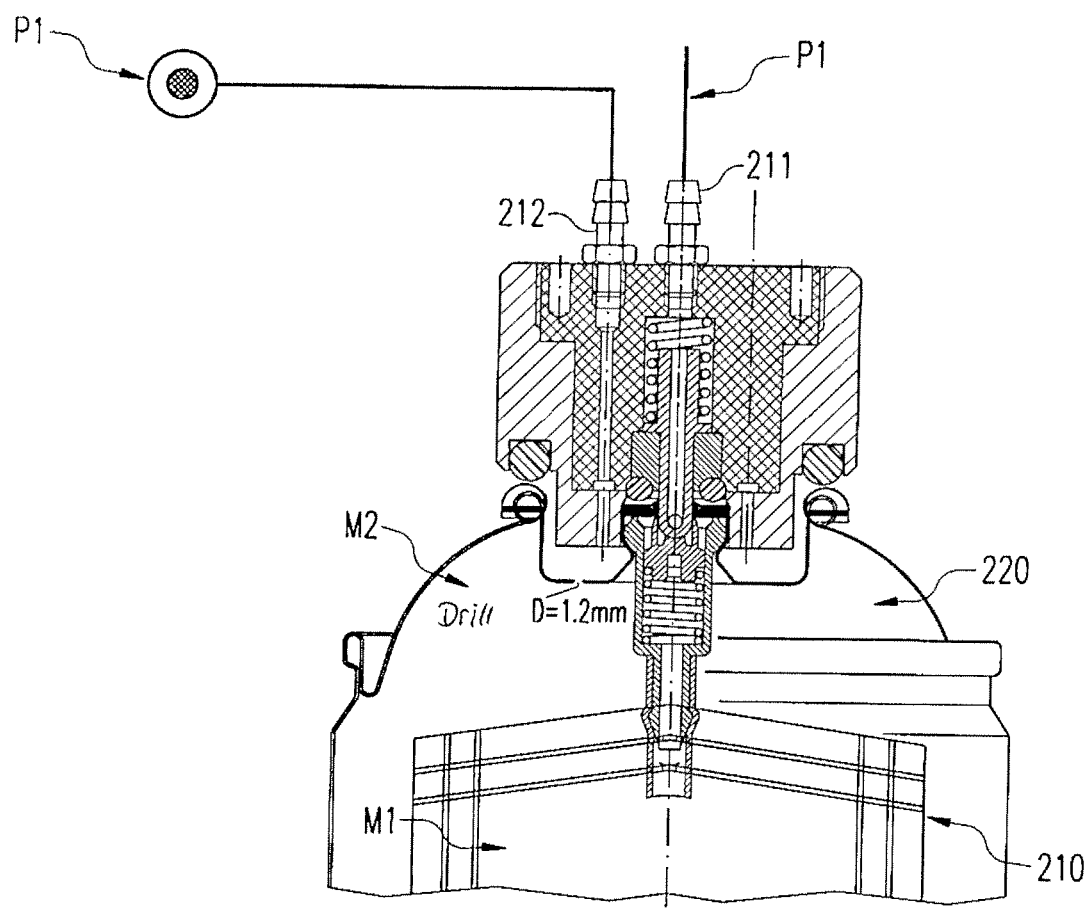

As is clear in particular from the example in FIG. 4, a receiving space 220 provided in the medium container 200 for the second medium M2 is in pressure exchange with a receiving space 210 for the first medium M1, wherein the receiving spaces 210, 220 are preferably separated from each other by a flexible material. In the illustrative embodiment described, the pressure exchange between the two receiving spaces 210, 220 is such that, between the two receiving spaces 210, 220, there is no difference in pressure of the first and second media M1, M2. Provision is particularly advantageously made that the receiving space 210 for the medium M1 comprises a flexible bag, which is preferably completely surrounded by the receiving space 220 for the second medium M2.

It is also conceivable that the medium container contains a large number of bags that are in pressure exchange with a second medium M2 surrounding the bags. The media in the bags can also preferably be chosen differently. It is particularly advantageous if the quantities of the first and second media M1, M2 are different, in which case, for example, the quantity of the second medium M2 can exceed the quantity of the first medium M1, so that, upon removal of a quantity of the first medium M1 from the medium container, the pressure P1 of the medium M2 is almost unchanged and can be transferred to the first medium M1.

In the illustrative embodiment in FIG. 4, the medium container 200 is formed by a spray can, which receives a first medium M1, in this case a maintenance oil for dental instruments. The spray can has a medium connector 211, which permits the exchange of the first medium M1 with the metering container 100.

In the illustrative embodiment in FIG. 1, the first and second regions V1, V2 in the metering container 100 are designed as a hollow space in a central body 110.

The first region V1 is connected by a valve VIN, preferably a non-return valve, to a medium container 200, in which a medium M1, the maintenance oil, is stored under pressure, such that the region V1 can determine a volume of the medium M1 to be measured off. The second region V2 has a supply line for another medium M2, in this case compressed air. The compressed-air source connected to the supply line is designed to provide compressed air on demand.

In a first step for removing a first medium M1 from the medium container 200, the second region V2 is subject only to the ambient air pressure, and a corresponding connector 212 of the second region V2 is in this case connected to the environment or to a corresponding pressure equivalent. The pressure P1 of the first medium M1, which exceeds the pressure in the second region V2, that is to say at this moment the air pressure, drives the medium M1 through the valve VIN, preferably designed as non-return valve, into the first region V1.

The movement range L (FIG. 3) of the separating element 120, which determines a maximum and minimum expansion of the first region V1, is in this case dimensioned so that the difference between maximum and minimum expansion of the first region V1 corresponds to the quantity of medium M1 to be measured off, in particular to a volume of the medium M1 to be measured off, so that the movement range L of the separating element 120 determines in particular a measurement volume or metering volume. Possible ways of optimizing the determination of the movement range L and therefore the determination of the measurement volume are described below.

In this first step, the separating element 120 is shifted in such a way that the first region V1 is maximized, i.e. the medium M1 is introduced into the region V1 designed as measurement volume. Maximized is to be understood in particular as meaning that no movement range L of the separating element 120 is available permitting an extension of the first region V1.

According to one aspect of the invention, the separating element 120 has a first contact face F1, which is directed towards the first region V1 and delimits or closes off the first region V1, and a second contact face F2, which is directed towards the second region V2 and delimits or closes off the second region V2. The first contact face F1 and the second contact face F2 have different surface dimensions. In particular, the separating element 120 is in contact with the media M1, M2 only via the first and second contact faces F1, F2, respectively. At equilibrium pressure, that is to say a pressure that acts identically on the boundary surfaces of the first and second regions V1 and V2, a difference force is established proportionally to the surface dimension difference D2-D1 of the contact faces F1 and F2. A corresponding detailed view of the metering container 100 with associated separating element 120 is shown for example in FIGS. 2 and 3.

As is clear from the illustrative embodiment shown, the separating element 120 is substantially freely movable in the metering container 100 and is in contact with the metering container 100 particularly preferably only via sealing elements 121, 122. In addition, provision can likewise be made that the separating element 120 is connected to a counterforce generator or itself has suitable means which, for example, interact with the central body 110 in such a way that a counterforce is produced.

Figure 2:
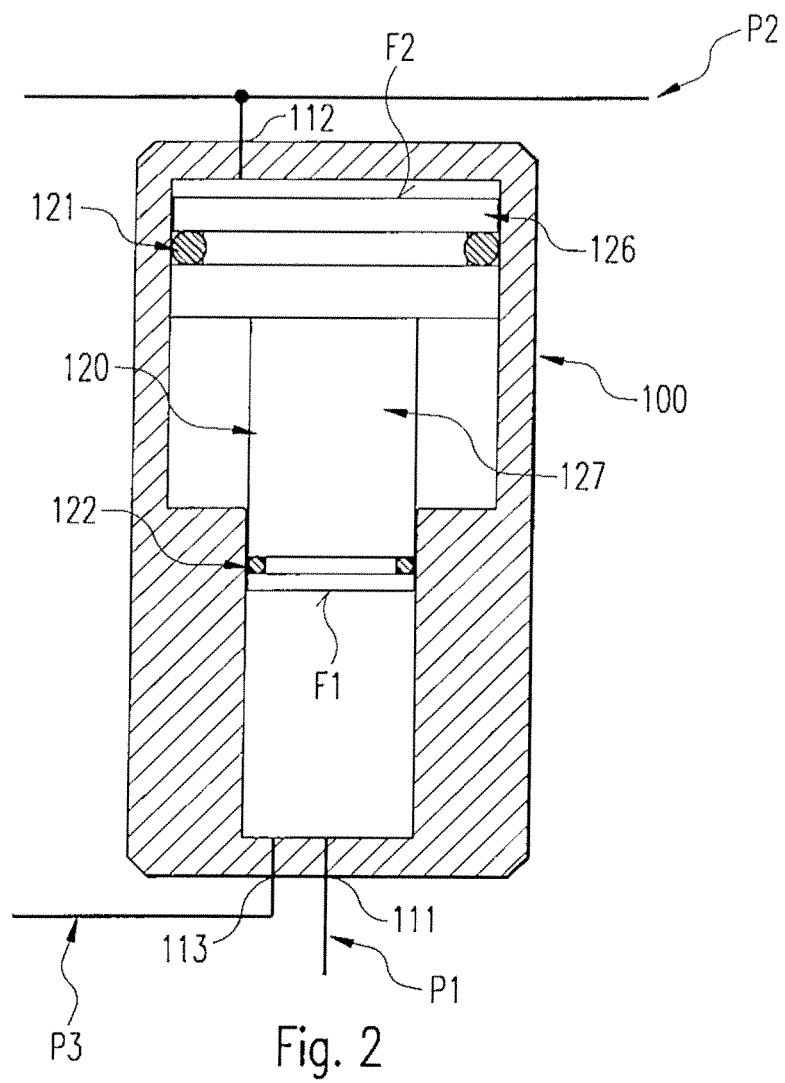
Figure 3:
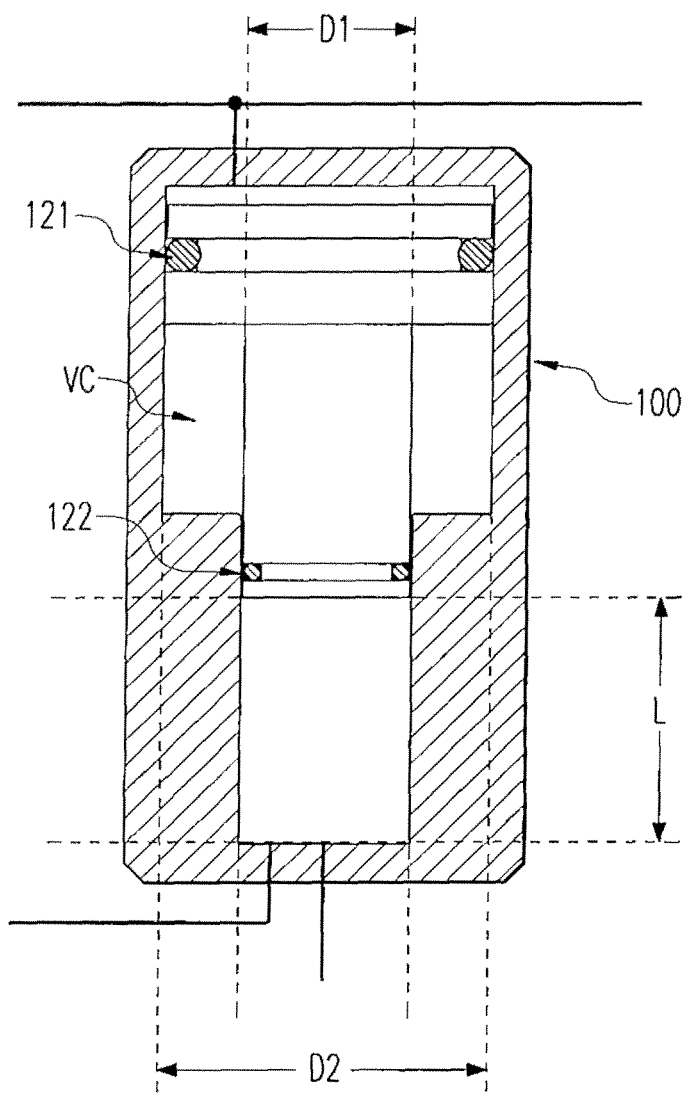

In the illustrative embodiment described, the separating element 120, which is in particular a linearly movable separating element 120, is in the form of a piston, as can be seen for example from FIGS. 2 and 3, which piston is movable in a recess, preferably a bore, in the central body 110 of the metering container 100.

It will be noted in particular that the shape of the recess is not limited to a bore with, for example, a round bore hole. Instead, any desired cross-sectional shape of the recess can be provided, and this can include, for example, polygonal cross sections, in particular rectangular, square, triangular or even elliptic cross sections. In a preferred development, the cross-sectional shapes in the first and second regions V1, V2 are different from each other.

The piston or separating element 120 comprises a first end-piece 126 and second end-piece 127, wherein the first end-piece 126 has a region that assumes the shape and expanse of a cross section of the bore or recess in the first region V1, and the second end-piece 127 has a region that assumes the shape and expanse of a cross section of the bore or recess in the second region V2. The surface of the first end-piece 126 directed towards the first region V1 establishes the contact face F1, and the surface of the second end-piece 127 directed towards the second region V2 establishes the contact face F2.

As is shown in FIG. 3, the first and second end-pieces 126, 127 each comprise sealing elements 121, 122 respectively, in particular sealing rings, which each provide a media-tight seal of the first and second regions V1, V2, in particular of the separating element 120 from the central body 110.

The separating element 120 or the piston is substantially freely movable in the metering container 100 and is in contact with the metering container 100 preferably only via the sealing elements 121, 122.

The sealing elements 121, 122 are preferably arranged at a distance from each other and thus at the same time provide a media-tight seal of a region VC between the first end-piece 126 and second end-piece 127.

The separating element 120 is preferably introduced into the central body 110 in such a way that the region VC is evacuated. For this purpose, the central body 110 has parts that engage with a form fit around the separating element 120 in the region between a first sealing element 121 and a second sealing element 122, such that, when fitted, the separating element can be brought into a position in which the region VC is substantially evacuated.

In one development, the central body, preferably in the transition region between the first and second regions V1, V2, is provided with a connector, which is connected to the region VC. Thus, for example, a reference medium can be brought into contact with the region VC or introduced into the region VC at a predetermined time, which reference medium generates a counterforce to the difference force at equilibrium pressure. For example, after the reference medium has been introduced, the region VC can be closed off or can remain open, so that a great many different counterforces with differing characteristics can be achieved, and a counterforce-generator is obtained in a simple way.

The illustrative embodiment depicted shows a piston with first and second end-pieces 126, 127 lying opposite each other, but it should be stressed that the invention is not limited to this embodiment, and instead different arrangement positions of the first and second end-pieces 126, 127 are conceivable. For example, the first or second end-piece can comprise a large number of separate contact faces F1 or F2, although the total extent thereof is still according to the invention. In particular, this embodiment also comprises pistons or separating elements 120 that are guided in a plurality of recesses.

If in a further step the medium M2 is introduced into the second region V2 at an identical pressure (P2=P1) to the pressure P1 of the medium M1 in the first region V1, then, in this illustrative embodiment, the force acting on the separating element 120 is of such a nature that the separating element 120 reaches a limit position, in which it minimizes the first region V1. By movement, in particular displacement, of the separating element 120, the medium M1 is driven out of the first region V1. In another embodiment, however, maximization can also be provided.

At equal pressure—the equilibrium pressure—in the first and second regions V1, V2, a difference force is obtained that is proportional to the surface difference of the first and second contact faces F1, F2 of the piston or of the separating element 120. In the illustrative embodiment, the first contact face F1 directed towards the first region V1 is smaller than the second contact face F2 directed towards the second region. Therefore, on account of the difference force, the piston or the separating element 120 is displaced in the direction of the first region V1 until the separating element 120, utilizing the movement range L, comes into contact with a boundary element, in this case with the central body 110, in a limit position. The first region V1, delimited by the recess and the separating element 120, has a minimal dimension in this position of the separating element 120, and the medium M1 is in this case substantially removed from the metering container or is reduced, in relation to a second limit position of the separating element 120, by the quantity of medium M1 that is to be measured off. As will be easily appreciated, a maximization of the first region V1 could be achieved by the contact face F1 being larger than the contact face F2 of the second region V2.

The movement range L of the separating element 120 is preferably limited by a boundary element, which in this case is obtained, in the transition region between the first and second regions V1, V2, by a different dimension of the recess or bore. However, as has already been indicated, a variation of the cross-sectional shape in the transition region could also form a boundary element. In addition, the boundary element could also be obtained independently of and spatially separate from the transition region of the first and second regions V1, V2, for example by a corresponding abutment that comes into contact with the piston or the separating element 120.

Through the equilibrium pressure (P1=P2), an operating point of the metering device 1 is obtained that is relatively easy to adjust. For example, the second medium M2 in the medium container 200 could be used for this purpose. An identical pressure source is preferably provided for the first medium M1 and second medium M2.

In one development, for example, the equilibrium pressure can be established by virtue of the fact that both the metering container 100 and also the medium container 200, in addition to having connectors 111, 211 forming a connection between the medium container 200 and the metering container 100, also have an additional medium connector 112, 212, respectively. In the illustrative embodiment described, the additional medium connector 112 of the metering container 100 is connected to the second region V2 of the metering container 100 for supplying the medium M2, and the additional medium connector 212 of the medium container 200 is connected to a receiving space 220 for the second medium M2 inside the medium container 200.

The respective additional medium connector 112, 212 is connected to a common supply line which serves for the supply of the second medium M2, in this case the compressed air. By way of this supply line, a pressure P2 can be generated both in the second region V2 of the metering container 100 and also in the receiving space 220 for the second medium M2. The pressure P2 of the second medium M2 in the receiving space 220 is transferred to the receiving space 210 for the first medium M1, so that the pressure P1 of the first medium M1 is identical to the pressure P2 of the second medium M2; the medium M1 is therefore in pressure synchronization with the medium M2, and an equilibrium pressure (P1=P2) is established. The unchanged pressure of the second medium M2 is thus used both to control the introduction of the first medium M1 into the metering container 100 and also to control the discharge of the measured-off quantity of the first medium M1 from the metering container 100. A reduction of the interacting parameters of the metering device 1 is thus achieved, and the metering result is therefore improved.

A further aspect of the invention proposes that, at an equilibrium pressure that acts identically on boundary surfaces of the first and second regions V1, V2, the separating element 120 experiences a force effect that is proportional or inversely proportional to the equilibrium pressure (P1=P2).

This is particularly advantageous if a first medium M1 to be metered is gaseous. With the aid of a counterforce generator or counter-pressure generator, which is formed for example by a gas introduced into the region VC, a self-regulating system can thus be achieved with which pressure fluctuations of the medium M1 are compensated by the fact that the first region V1 intended for the measuring-off or metering is limited by the displacement of the separating element 120, until a force equilibrium is established between a force proportional or inversely proportional to the equilibrium pressure and a counterforce. In this way it is possible to measure off constantly the quantity of a gas that is subject to pressure fluctuations.

In particular, with a counter-pressure generator, the force proportional to the equilibrium pressure can generate an inversely proportional force. In addition to the previously described example, other means are also conceivable as counter-pressure generator, for example a spring, a viscous medium, or even an electrically adjustable force, for example obtained by induction in interaction with the separating element 120.

To improve the expulsion or release of the first medium M1 from the metering container 100, provision is preferably made that at least one of the first and second regions V1, V2 has an inlet opening 111 and, preferably spatially separate from the latter, an outlet opening 113, wherein in particular the inlet opening 111 is connected to a first valve VIN, and the outlet opening 113 is preferably connected to a second valve VOUT. For the automatic control of the outlet of media, the working pressures of the first and second valves VIN and VOUT could be different.

Figure 5:
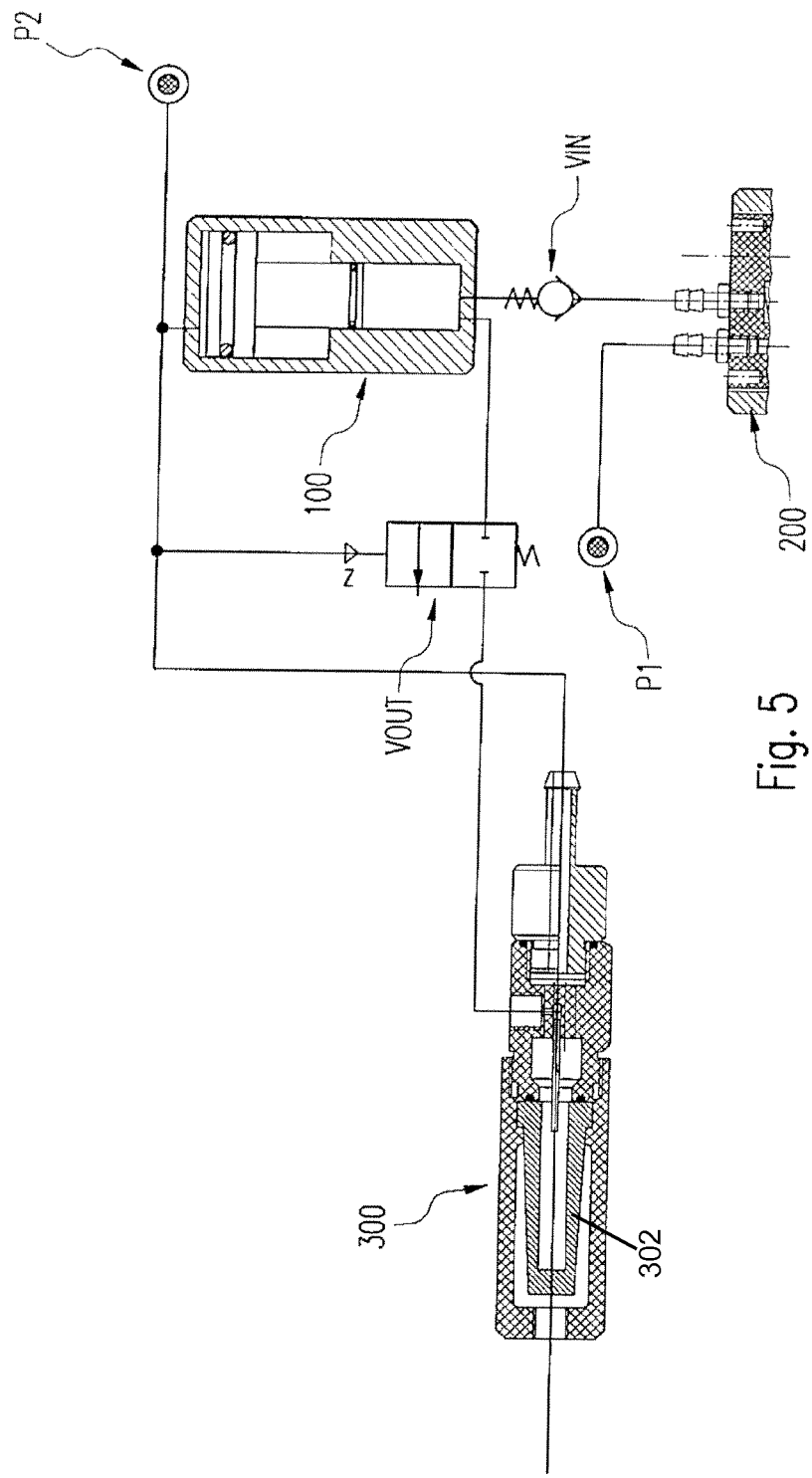

However, the second valve VOUT preferably has a control connector that permits an opening or closing of the valve when a control signal is present. In the illustrative embodiment shown, the control signal, as can be seen from FIGS. 1 and 5 for example, is likewise obtained through the pressure P2 of the second medium M2. The second valve VOUT is therefore connected to the second medium M2, in particular for the purpose of control.

Thus, opening of the second valve VOUT can be achieved time-synchronously with the application of the equilibrium pressure (P1=P2) to the metering container 100 by means of the medium M2. The valve VOUT is therefore controlled time-synchronously at the start of the expulsion of the medium M1, for example the maintenance oil.

The metering container 100 is connected by the second valve VOUT to an atomizer 300, so that the maintenance oil, i.e. the first medium M1, can now be sprayed via the atomizer 300 into the interior of a dental instrument, for example a dental handpiece.

The atomizer 300 has a sinter material, in particular a sinter filter 302, which is initially soaked with the maintenance oil, i.e. with the first medium M1. The quantity of maintenance oil (first medium M1) measured off by the metering device 1, in particular by the metering container 100, is chosen so that this quantity can be taken up completely and in its entirety by the sinter filter 302.

In addition, the atomizer 300 is likewise connected to the second medium M2, in particular to the compressed-air connector. The compressed air (other gases, as has already been indicated, could also be provided here) flows through the sinter filter 302 in such a way that the maintenance oil is driven out of the sinter filter 302 and is blown as a mist into a dental instrument, to ensure the intended maintenance of the instrument.

Thus, the second medium M2 likewise permits time-accurate control of the atomizer 300, which in addition also determines the pressure P1 of the first medium M1, i.e. of the maintenance oil, and thus minimizes the number of interacting parameters of the maintenance system and thereby improves the metering of the maintenance oil.

It remains to note that a further cycle of metering and atomization of the first medium M1 can be achieved by the compressed air being switched off and the compressed-air connectors of the atomizer 300, of the metering container 100 and also of the second valve VOUT being evacuated or placed under ambient pressure.

A method according to the invention for removing a medium M1 from a pressurized medium container 200, with a metering device 1 according to one aspect of the invention, thus involves a step of transferring a first medium M1 from the medium container 200 into a first region V1 of a metering container 100 until the first region V1 is completely filled, and a further step of driving the medium M1 out of the metering container 100 by filling the second region V2 with a second medium M2.

As is clear from the illustrative embodiment described, the pressure at which the second medium M2 is introduced into the metering container 100 does not exceed the pressure at which the first medium M1 is introduced into the metering container 100.

It will also be clear from what has been described above that a method for operating a disinfection and maintenance appliance for dental instruments proposes controlling a metering device 1 for a first medium M1 and at least one further device for discharging the first medium M1, in particular an atomizer 300, using a common pressurized medium, in particular the second medium M2, wherein in particular a timed coordination or control takes place.

It is thus clear that the invention makes available a disinfection and maintenance system for dental instruments, which system permits precise time control of the maintenance sequence and improved metering of a pressurized medium with the aid of a metering device 1 and thus considerably improves the disinfection and maintenance result. As the implementation in one common illustrative embodiment likewise shows, all aspects and developments of the invention can be combined with one another in any desired manner.

The invention claimed is:

1. A disinfection and maintenance system for medical or dental instruments, comprising:

a first medium selected from the group consisting of a dental instrument maintenance oil, a dental instrument cleaning solution, and a dental instrument disinfection liquid;

a medium container having a first receiving space, the first receiving space containing the first medium; and, a metering device for removing the first medium from the medium container, the metering device comprising:

a metering container designed to measure a quantity of the first medium, the metering container including a first region and a second region, the first region being adapted to receive the first medium from the medium container, the second region being adapted to receive a second medium under pressure; and a movable separating element separating the first region from the second region, the separating element including a first contact face directed toward the first region and which delimits or closes off the first region and a second contact face directed toward the second region and which delimits or closes off the second region;

wherein the first contact face and the second contact face oppose each other, and the movable separating element is designed such that, at one or more pressures that act on respective boundary surfaces of the first region and the second region, the movable separating element experiences a force effect from the one or more pressures such that the movable separating element moves within the metering container, and wherein the first contact face is smaller than the second contact face such that when the first medium has a first pressure, the second medium has a second pressure equal to or different from the first pressure, and the first pressure and the second pressure act on respective boundary surfaces of the first region and the second region, the movable separating element moves within the metering container, thereby driving the first medium out of the first region of the metering device.

2. The maintenance system according to claim 1, wherein the separating element is substantially freely movable in the metering container and is in contact with the metering container.

3. The maintenance system according to claim 2, wherein the separating element is in contact with the metering container only via sealing elements.

4. The maintenance system according to claim 1, wherein the separating element is formed by a piston, which is freely movable at least partially in a bore of the metering container.

5. The maintenance system according to claim 1, wherein at least one of the first region and the second region has an inlet opening and an outlet opening, wherein the inlet opening is connected to a first valve, and the outlet opening is connected to a second valve.

6. The maintenance system according to claim 5, wherein the inlet and outlet openings are spatially separate from each other.

7. The maintenance system according to claim 5, wherein working pressures of the first valve and the second valve differ from each other.

8. The maintenance system according to claim 1, wherein each of the metering container and the medium container, in addition to having connectors forming a connection between the medium container and the metering container, has an additional medium connector.

9. The maintenance system according to claim 1, wherein the first region is in pressure exchange with the second region, and the first region can be emptied with the aid of an external pressure, which acts on the second region.

10. The maintenance system according to claim 1, further comprising an atomizer connected to the metering container and configured to spray the first medium into a medical or dental instrument.

11. The maintenance system according to claim 10, wherein the atomizer is connected to a compressed-air connector.

12. The maintenance system according to claim 11, wherein the metering container is connected to the compressed-air connector.

13. The maintenance system according to claim 10, wherein the metering container is adapted to measure a quantity of the first medium that can be entirely taken up by a sinter filter in the atomizer.

14. The maintenance system according to claim 1, wherein the first medium is selected from the group consisting of the dental instrument maintenance oil and the dental instrument cleaning solution.

\* \* \* \* \*